US007976838B2

(12) United States Patent
Benyunes

(10) Patent No.: US 7,976,838 B2
(45) Date of Patent: *Jul. 12, 2011

(54) THERAPY OF AUTOIMMUNE DISEASE IN A PATIENT WITH AN INADEQUATE RESPONSE TO A TNF-α INHIBITOR

(75) Inventor: Mark C. Benyunes, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 450 days.

This patent is subject to a terminal disclaimer.

(21) Appl. No.: 12/052,606

(22) Filed: Mar. 20, 2008

(65) Prior Publication Data

US 2008/0213280 A1 Sep. 4, 2008

Related U.S. Application Data

(63) Continuation of application No. 10/818,765, filed on Apr. 6, 2004, now abandoned.

(60) Provisional application No. 60/461,481, filed on Apr. 9, 2003.

(51) Int. Cl.
*A61K 39/40* (2006.01)
*A61K 39/395* (2006.01)
*A61K 39/00* (2006.01)
*C07K 16/00* (2006.01)

(52) U.S. Cl. ........... 424/130.1; 424/133.1; 424/138.1; 424/141.1; 424/143.1; 424/144.1; 424/152.1; 424/153.1; 424/155.1; 424/156.1

(58) Field of Classification Search .................. None
See application file for complete search history.

(56) References Cited

U.S. PATENT DOCUMENTS

| | | | |
|---|---|---|---|
| 4,861,579 A | 8/1989 | Meyer et al. |
| 5,500,362 A | 3/1996 | Robinson et al. |
| 5,595,721 A | 1/1997 | Kaminski et al. |
| 5,645,817 A | 7/1997 | Seemann et al. |
| 5,677,180 A | 10/1997 | Robinson et al. |
| 5,721,108 A | 2/1998 | Robinson et al. |
| 5,736,137 A | 4/1998 | Anderson et al. |
| 5,776,456 A | 7/1998 | Anderson et al. |
| 5,843,398 A | 12/1998 | Kaminski et al. |
| 5,843,439 A | 12/1998 | Anderson et al. |
| 5,849,898 A | 12/1998 | Seed et al. |
| 6,015,542 A | 1/2000 | Kaminski et al. |
| 6,090,365 A | 7/2000 | Kaminski et al. |
| 6,120,767 A | 9/2000 | Robinson et al. |
| 6,171,586 B1 | 1/2001 | Lam et al. |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,287,537 B1 | 9/2001 | Kaminski et al. |
| 6,368,596 B1 | 4/2002 | Ghetie et al. |
| 6,399,061 B1 | 6/2002 | Anderson et al. |
| 6,410,391 B1 | 6/2002 | Zelsacher |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 7,708,994 B2 | 5/2010 | Benyunes |
| 7,820,161 B1 | 10/2010 | Curd et al. |
| 2002/0004587 A1 | 1/2002 | Miller et al. |
| 2002/0006404 A1 | 1/2002 | Hanna et al. |
| 2002/0009444 A1 | 1/2002 | Grillo-Lopez |
| 2002/0012665 A1 | 1/2002 | Hanna |
| 2002/0041847 A1 | 4/2002 | Goldenberg |
| 2002/0128488 A1 | 9/2002 | Yamakawa et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026801 A1 | 2/2003 | Weiner et al. |
| 2006/0024300 A1 | 2/2006 | Adams et al. |
| 2006/0034835 A1 | 2/2006 | Adams et al. |
| 2009/0155257 A1 | 6/2009 | Adams et al. |
| 2009/0238762 A1 | 9/2009 | Totoritis et al. |

FOREIGN PATENT DOCUMENTS

| | | |
|---|---|---|
| DE | 42 25 853 A 1 | 2/1994 |
| EP | 0 332 865 | 9/1989 |
| EP | 0 330 191 B1 | 10/1996 |
| EP | 1519959 A2 | 4/2005 |
| EP | 1613350 B1 | 3/2009 |
| WO | WO 92/22653 | 12/1992 |
| WO | WO 95/03770 | 2/1995 |
| WO | WO 98/56418 A2 | 12/1998 |
| WO | WO 98/58964 | 12/1998 |
| WO | WO 99/22764 | 5/1999 |
| WO | WO 99/51642 | 10/1999 |
| WO | WO 00/09160 A1 | 2/2000 |
| WO | WO 00/20864 | 4/2000 |
| WO | WO 00/27428 | 5/2000 |
| WO | WO 00/27433 | 5/2000 |
| WO | WO 00/42072 | 7/2000 |
| WO | WO 00/44788 | 8/2000 |
| WO | WO 00/67795 | 11/2000 |

(Continued)

OTHER PUBLICATIONS

American College of Rheumatology Subcommittee on Rheumatoid Arthritis Guidelines, "Guidelines for the Management of Rheumatoid Arthritis" *Arthritis and Rheumatism* 46(2):328-346 (Feb. 2002).
Anderson et al., "Expression of Human B Cell-Associated Antigens on Leukemias and Lymphomas: A Model of Human B Cell Differentiation" *Blood* 63(6):1424-1433 (1984).
C. Barbas III, et al., "In vitro evolution of a neutralizing human antibody to human immunodeficiency virus type 1 to enhance affinity and broaden strain cross-reactivity" *Proc. Natl Acad. Sci. USA* 91:3809-3813 (Apr 1994).
De Vita et al., "Efficacy of Selective B Cell Blockade in the Treatment of Rheumatoid Arthritis" *Arthritis and Rheumatism* 46(8):2029-2033 (Aug. 2002).
Demidem et al., "Chimeric Anti-CD20 (IDEC-C2B8) Monoclonal Antibody Sensitizes a B Cell Lymphoma Cell Line to Cell Killing by Cytotoxic Drugs" *Cancer Biotherapy & Radiopharmaceuticals* 12(3):177-186 (1997).

(Continued)

*Primary Examiner* — Chun Dahle
(74) *Attorney, Agent, or Firm* — Wendy M. Lee

(57) ABSTRACT

The present application describes therapy with antagonists which bind to B cell surface markers, such as CD20. In particular, the application describes the use of such antagonists to treat autoimmune disease in a mammal who experiences an inadequate response to a TNFα-inhibitor.

14 Claims, No Drawings

FOREIGN PATENT DOCUMENTS

| | | |
|---|---|---|
| WO | WO 00/67796 | 11/2000 |
| WO | WO 00/74718 | 12/2000 |
| WO | WO 00/76542 | 12/2000 |
| WO | WO 01/03734 | 1/2001 |
| WO | WO 01/10460 | 2/2001 |
| WO | WO 01/10461 | 2/2001 |
| WO | WO 01/10462 | 2/2001 |
| WO | WO 01/13945 | 3/2001 |
| WO | WO 01/72333 | 10/2001 |
| WO | WO 01/74388 | 10/2001 |
| WO | WO 01/77342 | 10/2001 |
| WO | WO 01/80884 | 11/2001 |
| WO | WO 01/97858 | 12/2001 |
| WO | WO 02/04021 | 1/2002 |
| WO | WO 02/34790 | 5/2002 |
| WO | WO 02/060955 | 8/2002 |
| WO | WO 02/079255 | 10/2002 |
| WO | WO 02/096948 | 12/2002 |
| WO | WO 02/102312 | 12/2002 |
| WO | 03/029296 A1 | 4/2003 |
| WO | WO 03/068821 A2 | 8/2003 |
| WO | WO 2004/003155 A2 | 1/2004 |
| WO | WO 2004/091657 A | 10/2004 |

OTHER PUBLICATIONS

Edwards and Cambridge, "Sustained Improvement in Rheumatoid Arthritis Following a Protocol Designed to Deplete B Lymphocytes" *Rheumatology* 40:205-211 (2001).

Edwards et al., "B-lymphocyte depletion therapy in rheumatoid arthritis and other autoimmune disorders" *Biochemical Society Transactions* 30(part 4):824-828 (2002).

Edwards et al., "Efficacy and safety of Rituximab, a B-cell targeted chimeric monoclonal antibody: A randomized, placebo-controlled trial in patients with rheumatoid arthritis" *Arthritis and Rheumatism* (Abstract #446) 46(9):S197 (2002).

Einfeld et al., "Molecular Cloning of the Human B Cell CD20 Receptor Predicts a Hydrophobic Protein with Multiple Transmembrane Domains" *EMBO Journal* 7(3):711-717 (1988).

H. Hogrefe, et al., "Creating Randomized Amino Acid Libraries with the QuikChange Multi Site-directed Mutagenesis Kit" *BioTechniques* 33(5):1158-1165 (Nov. 2002).

Higashida et al., "Safety and efficacy of rituximab in the treatment of refractory rheumatoid arthritis" *Presented at the annual meeting of the American Society of Hematology* (2003).

Higashida et al., "Treatment of DMARD-Refractory Rheumatoid Arthritis With Rituximab" *Annual Scientific Meeting of the American College of Rheumatology* (Abstract #LB11), New Orleans, LA (Oct. 2002).

Jenkins and Hardy, "Biological modifier therapy for the treatment of rheumatoid arthritis" *American Journal of the Medical Sciences* 323(4):197-205 (2002).

Kiesel et al., "Removal of cells from a malignant B-cell line from bone marrow with immunomagnetic beads and with complement and immunoglobulin switch variant mediated cytolysis" *Leukemia Research* 11(12):1119-1125 (1987).

Leandro et al., "An open study of B lymphocyte depletion in systemic lupus erythematosus" *Article and Rheumatism* 46(10):2673-2677 (Oct. 2002).

Leandro et al., "B Lymphocyte depletion in rheumatoid arthritis: early evidence for safety, efficacy and dose response" *Arthritis and Rheumatism* (#1905) 44(9):S370 (2001).

Levine and Pestronk, "IgM antibody-related polyneuropathies: B-cell depletion chemotherapy using Rituximab" *Neurology* 52(8):1701-1704 (May 12, 1999).

Maloney et al., "The Anti-Tumor Effect of Monoclonal Anti-CD20 Antibody (mAb) Therapy Includes Direct Anti-Proliferative Activity and Induction of Apoptosis in CD20 Positive Non-Hodgkin's Lymphoma (NHL) Cell Lines" *Blood* (Abstract #2535) 88(10):637a (1996).

Matthews, R., "Medical Heretics" *New Scientist* 170(2285):34-37 (Apr. 7, 2001).

Nadler et al., "B4, a human B lymphocyte-associated antigen expressed on normal, mitogen-activated, and malignant B lymphocytes" *J. Immunol.* 131(1):244-250 (Jul. 1983).

Nadler et al., "Diagnosis and treatment of human leukemias and lymphomas utilizing monoclonal antibodies" *Progress in Hematology*, Brown, E., Grune & Stratton, Inc. vol. XII:187-225 (1981).

Nadler, L., "B Cell/Leukemia Panel Workshop: Summary and Comments (Chap. 1)" *Leukocyte Typing II*, Reinherz et al., Springer Verlag vol. 2:3-37 and Appendix (1986).

Perrotta and Abuel, "Response of Chronic Relapsing ITP of 10 Years Duration to Rituximab" *Blood* (Abstract #3360) 92(10 Suppl. 1 Part 1-2):88b (1998).

R. Balint, et al., "Antibody engineering by parsimonious mutagenesis" *Gene* 137:109-118 (1993).

Reff et al., "Depletion of B Cells In Vivo by a Chimeric Mouse Human Monoclonal Antibody to CD20" *Blood* 83(2):435-445 (1994).

Stasi et al., "Rituximab chimeric anti-CD20 monoclonal antibody treatment for adults with chronic idiopathic thrombocytopenic purpura" *Blood* 98(4):952-957 (Aug. 15, 2001).

Tedder et al., "The B Cell Surface Molecule B1 is Functionally Linked with B Cell Activation and Differentiation" *The Journal of Immunology* 135(2):973-979 (Aug. 1985).

Tedder et al., "The CD20 Surface Molecule of B Lymphocytes Functions as a Calcium Channel" *J. Cell. Biochem.* (Abstract #M 023) 14D:195 (1990).

Tuscano et al., "A Phase I/II Trial of Rituxan(R) in Patients with Rheumatoid Arthritis" (Study No. U2109s) pp. 1-27 (Jan. 27, 2004).

Tuscano et al., "A Phase I/II Trial of Rituxan(R) in Patients with Rheumatoid Arthritis" (Study No. U2109s) pp. 1-27 (Oct. 17, 2000).

Tuscano et al., "Successful treatment of Infliximab-refractory rheumatoid arthritis with rituximab" *Annual Scientific Meeting of the American College of Rheumatology* (Presentation #LB11, poster #444, from OASIS—Online Abstract Submission and Invitation System), New Orleans, LA (Oct. 24-29, 2002).

Valentine et al., "Phosphorylation of the CD20 Phosphoprotein in Resting B Lymphocytes" *J. Bio. Chem.* 264(19):11282-11287 (1989).

Vaswani and Hamilton, "Humanized Antibodies as Potential Therapeutic Drugs" *Ann. Allergy, Asthma & Immunol.* 81(2):105-115, quiz 115-116, 119 (Aug. 1998).

Wei-Ping Yang, et al., "CDR walking mutagenesis for the affinity maturation of a potent human anti-hiv-1 antibody into the picomolar range" *J. Mol. Biol.* 254:392-403 (1995).

www.remicade-infliximab.com/pages/enbrel embrel.html.

"Definition of body surface area" (MedicineNet.com—http://www.medterms.com/script/main/art.asp?articlekey=39851) pp. 1-2 (2006).

Arthritis Research Campaign (arc), "Arc welcomes positive results from RA drug trial" (Press release on arc website www.arc.org.uk) pp. 1-3 (Oct. 2002).

Genentech, Inc., "Preliminary positive data from investigational randomized phase II trial demonstrates Rituxan as a potential treatment for rheumatoid arthritis" (press release) pp. 1-3 (Oct. 28, 2002).

Leandro et al., "Clinical outcome in 22 patients with rheumatoid arthritis treated with B Lymphocyte depletion" *Annals of the Rheumatic Diseases* 61(10):883-888 (2002).

Tuscano, "Successful treatment of infliximab-refractory rheumatoid arthritis with rituximab (Annual Scientific Meeting of the American College of Rheumatology, New Orleans, LA—Oct. 2002)" *Arthritis and rheumatism* (Presentation No. LB11) 46:3402 (2002).

www.remicade-infliximab.com/pages/enbrel_embrel.html, May 21, 2004, pp. 1-2.

van Vollenhoven, R., "Editorial: More or less rituximab? Biology and clinic, regulators and researchers" *Arthritis and Rheumatism* (Article accepted Nov. 9, 2010, not yet copyedited. http://onlinelibrary/wiley/com/doi/10.1002/art.30154/pdf) pp. 1-7 (2010).

Vital et al., "Reduced dose rituximab in rheumatoid arthritis: efficacy depends on degree of B cell depletion" *Arthritis and Rheumatism* (Article accepted Nov. 9, 2010, not yet copyedited. http://onlinelibrary.wiley.com/doi/10.1002/art.30152/pdf) pp. 1-18 (2010).

Anolik et al., "The relationship of FcβRIIIa genotype to degree of B cell depletion by rituximab in the treatment of systemic lupus erythematosus" *Arthritis and Rheumatism* 48(2):455-459 (Feb 2003).

Cannella and O'Dell, "Is there still a role for traditional disease-modifying antirheumatic drugs (DMARDs) in rheumatoid arthritis?" *Current Opinion in Rheumatology* 15(3):185-192 (May 2003).

Choy et al., "Therapeutic benefit of blocking interleukin-6 activity with an anti-interleukin-6 receptor monoclonal antibody in rheumatoid arthritis: a randomized, double-blind, placebo-controlled, dose-escalation trial" *Arthritis and Rheumatism* 46(12):3143-3150 (Dec. 2002).

Chustecka, Z., "Rituximab in RA: "we should aim for permanent remission"" *Medscape Medical News* (www.medscape.com/viewarticle/537826) pp. 1-3 (Jun. 16, 2004).

Cohen et al., "A multicentre, double blind, randomised, placebo controlled trial of anakinra (Kineret), a recombinant interleukin 1 receptor antagonist, in patients with rheumatoid arthritis treated with background methotrexate" *Ann. Rheum. Dis.* 63(9):1062-1068 (Sep. 2004).

Cohen et al., "Rituximab for rheumatoid arthritis refractory to anti-tumor necrosis factor therapy: Results of a multicenter, randomized, double-blind, placebo-controlled, phase III trial evaluating primary efficacy and safety at twenty-four weeks" *Arthritis Rheum.* 54(9):2793-2806 (2006).

Edwards and Cambridge, "Rheumatoid arthritis: the predictable effect of small immune complexes in which antibody is also antigen" *Br. J. Rheumatol.* 37(2):126-130 (Feb. 1998).

Edwards et al., "Efficacy of B-cell-targeted therapy with rituximab in patients with rheumatoid arthritis" *New England J. of Medicine* 350(25):2572-2581 (Jun. 17, 2004).

Felson at al., "American College of Rheumatology. Preliminary definition of improvement in rheumatoid arthritis" *Arthritis Rheum.* 38(6):727-735 (Jun. 1995).

Gremillion and van Vollenhoven, "Rheumatoid arthritis, Designing and implementing a treatment plan" *Postgrad. Med.* 103(2):103-106, 110, 116-118, 121-123 (Feb. 1998).

Gunnarsson et al., "Histopathologic and clinical outcome of rituximab treatment in patients with cyclophosphamide-resistant proliferative lupus nephritis" *Arthritis Rheum.* 56(4):1263-1272 (Apr. 2007).

Lard et al., "Early versus delayed treatment in patients with recent-onset rheumatoid arthritis: comparison of two cohorts who received different treatment strategies" *Am. J. Med.* 111(6):446-451 (Oct. 15, 2001).

MabThera EU Summary of Product Characteristics (SMPC) pp. 1-85 (2010).

Maini et al., "Infliximab (chimeric anti-tumour necrosis factor α monoclonal antibody) versus placebo in rheumatoid arthritis patients receiving concomitant methotrexate: a randomised phase III trial. ATTRACT Study Group" *Lancet* 354:1932-1939 (Dec. 1999).

Maini et al., "Therapeutic efficacy of multiple intravenous infusions of anti-tumor necrosis factor α monoclonal antibody combined with low-dose weekly methotrexate in rheumatoid arthritis" *Arthritis and Rheumatism* 41(9):1552-1563 (1998).

Moreland et al., "Double-blind, placebo-controlled multicenter trial using chimeric monoclonal anti-CD4 antibody, cM-T412, in rheumatoid arthritis patients receiving concomitant methotrexate" *Arthritis Rheum.* 38(11):1581-1588 (Nov. 1995).

Olsen et al., "A double-blind, placebo-controlled study of anti-CD5 immunoconjugate in patients with rheumatoid arthritis. The Xoma RA Investigator Group" *Arthritis Rheum.* 39(7):1102-1108 (Jul. 1996).

Rigby et al., "Rituximab (RTX) improved physical function and quality of life in patients with early RA: results from a randomized active comparator placebo-controlled trial of RTX in comb. with MTX compared to MTX alone in patients naive to MTX (IMAGE)" (Poster SAT0121, EULAR Copenhagen, DK Jun. 10-13, 2009).

Rigby et al., "Rituximab improved physical function and quality of life in patients with early RA: results from a randomized active comparator placebo-controlled trial of rituximab in combination with MTX compared to MTX alone in pat" *Ann. Rheum. Dis.* (Abs SAT0121) 68(Sup 3):581 (2009).

Rigby et al., "Rituximab improved physical function and quality of life in patients with early rheumatoid arthritis who were naive to methotrexate (IMAGE study)" (Poster 1665 presented at American College of Rheumatology-ACR/ARHP Scientific Meeting, Philadelphia, PA Oct. 16-21, 2009) pp. 1.

Smolen et al., "Consensus statement on the use of rituximab in patients with rheumatoid arthritis" *Annals of the Rheumatic Diseases* 66(2):143-150 (Feb. 2007).

Strand and Lee, "Differential patterns of response in patients with rheumatoid arthritis following administration of an anti-CD 5 immunoconjugate" *Clin. Exp. Rheumatol.* 11(Suppl 8):S161-5163 (Mar.-Apr. 1993).

Strand et al., "Treatment of active rheumatoid arthritis with leflunomide compared with placebo and methotrexate. Leflunomide Rheumatoid Arthritis Investigators Group" *Arch Intern Med.* 159 (21):2542-2550 (Nov. 1999).

Tak et al., "Inhibition of joint damage and improved clinical outcomes with a combination of rituximab and methotrexate (MTX) in patients with early active RA who are naive to MTX: a randomised active comparator placebo-controlled trial" *Ann. Rheum. Dis.* (Abs OP-0022) 68(Suppl 3):75 (2009).

Tak et al., "Inhibition of joint damage and improved clinical outcomes with a combination of rituximab and MTX in patients with early active RA who are naive to MTX: a randomised active comparator placebo-controlled trial (Image)" (EULAR Congress Poster, Rome, Italy, Jun. 16-19, 2010) pp. 1-32.

Tak et al., "Rituximab in combination with methotrexate (MTX) significantly inhibits joint damage in patients with early active RA who are naive to MTX: two-year radiographic outcomes from a randomized, active comparator, placebo-controlled trial (IMAGE)" *Ann. Rheum. Dis.* (Abs. OP0049) 69(Suppl 3):67 (2010).

U.S. Prescribing Information for etanercept/ENBREL pp. 1-26 (Sep. 2010).

U.S. Prescribing Information for Rituximab/RITUXAN pp. 1-35 (Feb. 2010).

van Leeuwen et al., "Interrelationship of outcome measures and process variables in early rheumatoid arthritis. A comparison of radiologic damage, physical disability, joint counts, and acute phase reactants" *J. Rheumatol.* 21(3):425-429 (Mar. 1994).

van Vollenhoven et al., "Treatment with infliximab (Remicade) when etanercept (Enbrel) has failed or vice versa: data from the STURE registry showing that switching tumour necrosis factor α blockers can make sense" *Ann. Rheum. Dis.* 62(12):1195-1198 (Dec. 2003).

van Vollenhoven, R., "Declaration of Ronald F. van Vollenhoven" (Filed in EP1613350 opposition, Annex A and B attached.) pp. 1-11 (Oct. 6, 2010).

van Vollenhoven, R., "Declaration under 37 C.F.R. 1.132" (Filed on Aug. 7, 2007 in U.S. Appl. No. 09/564,288; CV and bibliography of published papers attached) pp. 1-11 (Jul. 30, 2007).

van Vollenhoven, R., "Second Declaration of Dr. Ronald van Vollenhoven" (Filed on Feb. 23, 2010 in U.S. Appl. No. 09/564,288) pp. 1-6 (Jan. 19, 2010).

Vital et al., "A randomised double-blind placebo controlled trial on the effects of increased dose rituximab in patients with initial incomplete depletion" *Ann. Rheum. Dis.* (Abs. OP0275) 69(Suppl 3):147 (2010).

Vital et al., "Management of nonresponse to rituximab in rheumatoid arthritis, predictors and outcome of re-treatment" *Arthritis and Rheumatism* 62(5):1273-1279 (May 2010).

Weinblatt et al., "A Trial of Etanercept, a Recombinant Tumor Necrosis Factor Receptor: Fc Fusion Protein, in Patients with Rheumatoid Arthritis Receiving Methotrexate" *New England J. of Medicine* 340(4):253-259 (1999).

Weinblatt, M., "Declaration by Michael Weinblatt" (Submitted in opposition proceedings involving EP1176981. CV attached.) pp. 1-5 (Jul. 8, 2008).

THERAPY OF AUTOIMMUNE DISEASE IN A PATIENT WITH AN INADEQUATE RESPONSE TO A TNF-α INHIBITOR

This is a continuation application which claims priority under 35 USC §120 to non-provisional application no. 10/818,765, filed Apr. 6, 2004 (now abandoned), which claims priority under 35 USC §119 to provisional application no. 60/461,481 filed Apr. 9, 2003, the entire disclosures of which are hereby incorporated by reference.

FIELD OF THE INVENTION

The present invention concerns therapy with antagonists which bind to B cell surface markers, such as CD20. In particular, the invention concerns the use of such antagonists to treat autoimmune disease in a mammal who experiences an inadequate response to a TNFα-inhibitor.

BACKGROUND OF THE INVENTION

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

The CD20 antigen (also called human B-lymphocyte-restricted differentiation antigen, Bp35) is a hydrophobic transmembrane protein with a molecular weight of approximately 35 kD located on pre-B and mature B lymphocytes (Valentine et al. *J. Biol. Chem.* 264(19):11282-11287 (1989); and Einfeld et al. *EMBO J.* 7(3):711-717 (1988)). The antigen is also expressed on greater than 90% of B cell non-Hodgkin's lymphomas (NHL) (Anderson et al. *Blood* 63(6):1424-1433 (1984)), but is not found on hematopoietic stem cells, pro-B cells, normal plasma cells or other normal tissues (Tedder et al. *J. Immunol.* 135(2):973-979 (1985)). CD20 regulates an early step(s) in the activation process for cell cycle initiation and differentiation (Tedder et al., supra) and possibly functions as a calcium ion channel (Tedder et al. *J. Cell. Biochem.* 14D:195 (1990)).

Given the expression of CD20 in B cell lymphomas, this antigen can serve as a candidate for "targeting" of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to the neoplastic B cells. Irrespective of the approach, a primary goal is to destroy the tumor; the specific approach can be determined by the particular anti-CD20 antibody which is utilized and, thus, the available approaches to targeting the CD20 antigen can vary considerably.

CD19is another antigen that is expressed on the surface of cells of the B lineage. Like CD20, CD19 is found on cells throughout differentiation of the lineage from the stem cell stage up to a point just prior to terminal differentiation into plasma cells (Nadler, L. *Lymphocyte Typing II* 2: 3-37 and Appendix, Renling et al. eds. (1986) by Springer Verlag). Unlike CD20 however, antibody binding to CD19 causes internalization of the CD19 antigen. CD19 antigen is identified by the HD237-CD19 antibody (also called the "B4" antibody) (Kiesel et al. *Leukemia Research II*, 12: 1119 (1987)), among others. The CD19 antigen is present on 4-8% of peripheral blood mononuclear cells and on greater than 90% of B cells isolated from peripheral blood, spleen, lymph node or tonsil. CD19 is not detected on peripheral blood T cells, monocytes or granulocytes. Virtually all non-T cell acute lymphoblastic leukemias (ALL), B cell chronic lymphocytic leukemias (CLL) and B cell lymphomas express CD19 detectable by the antibody B4 (Nadler et al. *J. Immunol.* 131:244 (1983); and Nadler et al. in *Progress in Hematology Vol. XII pp.* 187-225. Brown, E. ed. (1981) by Grune & Stratton, Inc).

Additional antibodies which recognize differentiation stage-specific antigens expressed by cells of the B cell lineage have been identified. Among these are the B2 antibody directed against the CD21 antigen; B3 antibody directed against the CD22 antigen; and the J5 antibody directed against the CD10 antigen (also called CALLA). See U.S. Pat. No. 5,595,721 issued Jan. 21, 1997 (Kaminski et al.).

The rituximab (RITUXAN®) antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). RITUXAN® is indicated for the treatment of patients with relapsed or refractory low-grade or follicular, CD20 positive, B cell non-Hodgkin's lymphoma. In vitro mechanism of action studies have demonstrated that RITUXAN® binds human complement and lyses lymphoid B cell lines through complement-dependent cytotoxicity (CDC) (Reff et al. *Blood* 83(2):435-445 (1994)). Additionally, it has significant activity in assays for antibody-dependent cellular cytotoxicity (ADCC). More recently, RITUXAN® has been shown to have anti-proliferative effects in tritiated thymidine incorporation assays and to induce apoptosis directly, while other anti-CD19 and CD20 antibodies do not (Maloney et al. *Blood* 88(10):637a (1996)). Synergy between RITUXAN® and chemotherapies and toxins has also been observed experimentally. In particular, RITUXAN® sensitizes drug-resistant human B cell lymphoma cell lines to the cytotoxic effects of doxorubicin, CDDP, VP-16, diphtheria toxin and ricin (Demidem et al. *Cancer Biotherapy & Radiopharmaceuticals* 12(3):177-186 (1997)). In vivo preclinical studies have shown that RITUXAN® depletes B cells from the peripheral blood, lymph nodes, and bone marrow of cynomolgus monkeys, presumably through complement and cell-mediated processes (Reff et al. *Blood* 83(2):435-445 (1994)).

Patents and patent publications concerning CD20 antibodies include U.S. Pat. Nos. 5,776,456, 5,736,137, 6,399,061, and 5,843,439, as well as US patent appln nos. US 2002/0197255A1 and US 2003/0021781A1 (Anderson et al.); U.S. Pat. No. 6,455,043B1 and WO00/09160 (Grillo-Lopez, A.); WO00/27428 (Grillo-Lopez and White); WO00/27433 (Grillo-Lopez and Leonard); WO00/44788 (Braslawsky et al.); WO01/10462 (Rastetter, W.); WO01/10461 (Rastetter and White); WO01/10460 (White and Grillo-Lopez); US appln no. US2002/0006404 and WO02/04021 (Hanna and Hariharan); US appln no. US2002/0012665 A1 and WO01/74388 (Hanna, N.); US appln no. US2002/0009444A1, and WO01/80884 (Grillo-Lopez, A.); WO01/97858 (White, C.); US appln no. US2002/0128488A1 and WO02/34790 (Reff, M.); WO02/060955 (Braslawsky et al.); WO2/096948 (Braslawsky et al.); WO02/079255 (Reff and Davies); U.S. Pat. No. 6,171,586B1, and WO98/56418 (Lam et al.); WO98/58964 (Raju, S.); WO99/22764 (Raju, S.); WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.); WO00/42072 (Presta, L.); WO00/67796 (Curd et al.); WO01/03734 (Grillo-Lopez et al.); US appln no. US 2002/0004587A1 and WO01/77342 (Miller and Presta); US appln no. US2002/0197256 (Grewal, I.); U.S. Pat. Nos. 6,090,365B1, 6,287,537B1, 6,015,542, 5,843,398, and 5,595,721, (Kaminski et al.); U.S. Pat. Nos. 5,500,362, 5,677,180, 5,721,108, and 6,120,767(Robinson et al.); U.S. Pat. No. 6,410,391B1 (Raubitschek et al.); U.S. Pat. No. 6,224,866B1 and WO00/20864 (Barbera-Guillem, E.); WO01/13945 (Barbera-Guillem, E.); WO00/67795 (Goldenberg); WO00/74718 (Goldenberg and Hansen); WO00/76542 (Golay et al.); WO01/72333 (Wolin and Rosenblatt); U.S. Pat. No. 6,368,596B1 (Ghetie et al.); US Appln no. US2002/0041847A1, (Goldenberg, D.); US Appln no. US2003/0026801A1 (Weiner and Hartmann); WO02/102312 (Engleman, E.), each of which is expressly incorporated herein by reference. See, also, U.S. Pat. No. 5,849,898 and EP appln no. 330,191 (Seed et al.); U.S. Pat. No. 4,861,579 and EP332,865A2 (Meyer and Weiss); and WO95/03770 (Bhat et al.).

Publications concerning therapy with Rituximab include: Perrotta and Abuel "Response of chronic relapsing ITP of 10 years duration to Rituximab" Abstract # 3360 *Blood* 10(1) (part 1-2): p. 88B (1998); Stasi et al. "Rituximab chimeric anti-CD20 monoclonal antibody treatment for adults with chronic idopathic thrombocytopenic purpura" *Blood* 98(4): 952-957 (2001); Matthews, R. "Medical Heretics" New Scientist (7 Apr., 2001); Leandro et al. "Clinical outcome in 22 patients with rheumatoid arthritis treated with B lymphocyte depletion" Ann Rheum Dis 61:833-888 (2002); Leandro et al. "Lymphocyte depletion in thrumatoid arthritis: early evidence for safety, efficacy and dose response. *Arthritis and Rheumatism* 44(9): S370 (2001); Leandro et al. "An open study of B lymphocyte depletion in systemic lupus erythematosus", *Arthritis & Rheumatism* 46(1):2673-2677 (2002); Edwards and Cambridge "Sustained improvement in rheumatoid arthritis following a protocol designed to deplete B lymphocytes" *Rhematology* 40:205-211 (2001); Edwards et al. "B-lymphocyte depletion therapy in rheumatoid arthritis and other autoimmune disorders" Biochem. Soc. Trans. 30(4):824-828 (2002); Edwards et al. "Efficacy and safety of Rituximab, a B-cell targeted chimeric monoclonal antibody: A randomized, placebo controlled trial in patients with rheumatoid arthritis. Arthritis and Rheumatism 46(9): S197 (2002); Levine and Pestronk "IgM antibody-related polyneuropathies: B-cell depletion chemotherapy using Rituximab" Neurology 52: 1701-1704 (1999); DeVita et al. "Efficacy of selective B cell blockade in the treatment of rheumatoid arthritis" *Arthritis & Rheum* 46:2029-2033 (2002); Hidashida et al. "Treatment of DMARD-Refractory rheumatoid arthritis with rituximab." Presented at the Annual Scientific Meeting of the American College of Rheumatology; October 24-29; New Orleans, La. 2002; Tuscano, J. "Successful treatment of Infliximab-refractory rheumatoid arthritis with rituximab" Presented at the Annual Scientific Meeting of the American College of Rheumatology; October 24-29; New Orleans, La. 2002.

Rhematoid arthritis (RA) is an autoimmune disorder of unknown etiology. Most RA patients suffer a chronic course of disease that, even with therapy, may result in progressive joint destruction, deformity, disability and even premature death. More than 9 million physician visits and more than 250,000 hospitalizations per year result from RA. The goals of RA therapy are to prevent or control joint damage, prevent loss of function and decrease pain. Initial therapy of RA usually involves administration of one or more of the following drugs: nonsteroidal antiinflammatory drugs (NSAIDs), glucocorticoid (via joint injection), and low-dose prednisone. See "Guidelines for the management of rheumatoid arthritis" *Arthritis & Rheumatism* 46(2): 328-346 (February, 2002). The majority of patients with newly diagnosed RA are started with disease-modifying antirheumatic drug (DMARD) therapy within 3 months of diagnosis. DMARDs commonly used in RA are hydroxycloroquine, sulfasalazine, methotrexate, leflunomide, etanercept, infliximab (plus oral and subcutaneous methrotrexate), azathioprine, D-penicillamine, Gold (oral), Gold (intramuscular), minocycline, cyclosporine, Staphylococcal protein A immunoadsorption.

Because the body produces tumor necrosis factor alpha (TNFα) during RA, TNFα inhibitors have used for therapy of that disease.

Etanercept (ENBREL®) is an injectable drug approved in the US for therapy of active RA. Etanercept binds to TNFα and serves to remove most TNFα from joints and blood, thereby preventing TNFα from promoting inflammation and other symptoms of rheumatoid arthritis. Etanercept is an "immunoadhesin" fusion protein consisting of the extracellular ligand binding portion of the human 75 kD (p75) tumor necrosis factor receptor (TNFR) linked to the Fc portion of a human IgG1. The drug has been associated with negative side effects including serious infections and sepsis, nervous system disorders such as multiple sclerosis (MS). See, e.g., www.remicade-infliximab.com/pages/enbrel_embrel.html Infliximab, sold under the trade name REMICADE®, is an immune-suppressing drug prescribed to treat RA and Crohn's disease. Infliximab is a chimeric monoclonal antibody that binds to TNFα and reduces inflammation in the body by targeting and binding to TNFα which produces inflammation. Infliximab has been linked to a fatal reactions such as heart failure and infections including tuberculosis as well as demyelination resulting in MS.

In December 2002, Abbott Laboratories received FDA approval to market adalimumab (HUMIRA™), previously known as D2E7. Adalimumab is a human monoclonal antibody that binds to TNFα and is approved for reducing the signs and symptoms and inhibiting the progression of structural damage in adults with moderately to severely active RA who have had insufficient response to one or more traditional disease modifying DMARDs.

SUMMARY OF THE INVENTION

The present invention provides, in a first aspect, a method of treating an autoimmune disease in a mammal who experiences an inadequate response to a TNFα-inhibitor, comprising administering to the mammal a therapeutically effective amount of an antagonist which binds to a B cell surface marker.

For instance, the invention provides a method of treating rheumatoid arthritis in a mammal who experiences an inadequate response to a TNFα-inhibitor, comprising administering to the mammal a therapeutically effective amount of an antibody that binds to CD20.

The invention also concerns a method of reducing the risk of a negative side effect selected from the group consisting of an infection, heart failure and demyelination, comprising administering to a mammal with an autoimmune disease a therapeutically effective amount of an antagonist which binds to a B cell surface marker.

DETAILED DESCRIPTION OF THE PREFERRED EMBODIMENTS

I. Definitions

For the purposes herein, "tumor necrosis factor alpha (TNFα)" refers to a human TNFα molecule comprising the amino acid sequence as described in Pennica et al., *Nature*, 312:721 (1984) or Aggarwal et al., *JBC*, 260:2345 (1985).

A "TNFα inhibitor" herein is an agent that inhibits, to some extent, a biological function of TNFα, generally through binding to TNFα and neutralizing its activity. Examples of TNF inhibitors specifically contemplated herein are Etanercept (ENBREL®), Infliximab (REMICADE®) and Adalimumab (HUMIRA™).

The term "inadequate response to a TNFα-inhibitor" refers to an inadequate response to previous or current treatment with a TNFα-inhibitor because of toxicity and/or inadequate efficacy. The inadequate response can be assessed by a clinician skilled in treating the disease in question.

A mammal who experiences "toxicity" from previous or current treatment with the TNFα-inhibitor experiences one or more negative side-effects associated therewith such as infection (especially serious infections), congestive heart failure, demyelination (leading to multiple sclerosis), hypersensitivity, neurologic events, autoimmunity, non-Hodgkin's lymphoma, tuberculosis (TB), autoantibodies, etc.

A mammal who experiences "inadequate efficacy" continues to have active disease following previous or current treatment with a TNFα-inhibitor. For instance, the patient may have active disease activity after 1 month or 3 months of therapy with the TNFα-inhibitor.

By "reducing the risk of a negative side effect" is meant reducing the risk of a side effect resulting from therapy with the antagonist that binds to a B-cell surface marker to a lower extent than that seen with therapy with a TNFα-inhibitor. Such side effects include infection (especially serious infections), heart failure, and demyelination (multiple sclerosis), etc.

A "B cell surface marker" herein is an antigen expressed on the surface of a B cell which can be targeted with an antagonist which binds thereto. Exemplary B cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers. The B cell surface marker of particular interest is preferentially expressed on B cells compared to other non-B cell tissues of a mammal and may be expressed on both precursor B cells and mature B cells. In one embodiment, the marker is one, like CD20 or CD19, which is found on B cells throughout differentiation of the lineage from the stem cell stage up to a point just prior to terminal differentiation into plasma cells. The preferred B cell surface markers herein is CD20.

The "CD20" antigen is a ~35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35". The CD20 antigen is described in Clark et al. *PNAS* (*USA*) 82:1766 (1985), for example.

An "autoimmune disease" herein is a disease or disorder arising from and directed against an individual's own tissues. Examples of autoimmune diseases or disorders include, but are not limited to arthritis (rheumatoid arthritis, juvenile rheumatoid arthritis, osteoarthritis, psoriatic arthritis), psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), coronary artery disease etc.

An "antagonist" is a molecule which, upon binding to a B cell surface marker, destroys or depletes B cells in a mammal and/or interferes with one or more B cell functions, e.g. by reducing or preventing a humoral response elicited by the B cell. The antagonist preferably is able to deplete B cells (i.e. reduce circulating B cell levels) in a mammal treated therewith. Such depletion may be achieved via various mechanisms such antibody-dependent cell-mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native sequence peptides and small molecule antagonists which bind to the B cell marker, optionally conjugated with or fused to a cytotoxic agent. The preferred antagonist comprises an antibody.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and carry out ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refer to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Growth inhibitory" antagonists are those which prevent or reduce proliferation of a cell expressing an antigen to which the antagonist binds. For example, the antagonist may prevent or reduce proliferation of B cells in vitro and/or in vivo.

Antagonists which "induce apoptosis" are those which induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the amino acid residues of an antibody which are responsible for antigen-binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196: 901-917 (1987)). "Framework" or "FR" residues are those variable domain residues other than the hypervariable region residues as herein defined.

An antagonist "which binds" an antigen of interest, e.g. a B cell surface marker, is one capable of binding that antigen with sufficient affinity and/or avidity such that the antagonist is useful as a therapeutic agent for targeting a cell expressing the antigen.

Examples of antibodies which bind the CD20 antigen include: "C2B8" which is now called "rituximab" ("RITUXAN®") (U.S. Pat. No. 5,736,137, expressly incorporated herein by reference); the yttrium-[90]-labeled 2B8 murine antibody designated "Y2B8" (U.S. Pat. No. 5,736,137, expressly incorporated herein by reference); murine IgG2a "B1" optionally labeled with $^{131}$I to generate the "$^{131}$I-B1" antibody (BEXXAR™) (U.S. Pat. No. 5,595,721, expressly incorporated herein by reference); murine monoclonal antibody "1F5" (Press et al. *Blood* 69(2):584-591 (1987)); "chimeric 2H7 antibody" (U.S. Pat. No. 5,677,180, expressly incorporated herein by reference); "humanized 2H7 v16" (see below); huMax-CD20 (Genmab, Denmark); AME-133 (Applied Molecular Evolution); and monoclonal antibodies L27, G28-2, 93-1B3, B-C1 or NU-B2 available from the International Leukocyte Typing Workshop (Valentine et al., In: *Leukocyte Typing III* (McMichael, Ed., p. 440, Oxford University Press (1987)).

Examples of antibodies which bind the CD19 antigen include the anti-CD19 antibodies in Hekman et al. *Cancer Immunol. Immunother.* 32:364-372 (1991) and Vlasveld et al. *Cancer Immunol. Immunother.* 40:37-47 (1995); and the B4 antibody in Kiesel et al. *Leukemia Research II*, 12: 1119 (1987).

The terms "rituximab" or "RITUXAN®" herein refer to the genetically engineered chimeric murine/human monoclonal antibody directed against the CD20 antigen and designated "C2B8" in U.S. Pat. No. 5,736,137, expressly incorporated herein by reference. The antibody is an IgG$_1$ kappa immunoglobulin containing murine light and heavy chain variable region sequences and human constant region sequences. Rituximab has a binding affinity for the CD20 antigen of approximately 8.0 nM.

Purely for the purposes herein, "humanized 2H7 v16" refers to an antibody comprising the variable light and variable heavy sequences shown below.

Variable light-chain domain of hu2H7 v16

(SEQ ID NO: 1)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKR

Variable heavy-chain domain of hu2H7 v16

(SEQ ID NO: 2)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSS

Preferably humanized 2H7 v16 comprises the light chain amino acid sequence (SEQ ID NO: 3)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC;

and heavy chain amino acid sequence (SEQ ID NO: 4)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK.

An "isolated" antagonist is one which has been identified and separated and/or recovered from a component of its natural environment. Contaminant components of its natural environment are materials which would interfere with diagnostic or therapeutic uses for the antagonist, and may include enzymes, hormones, and other proteinaceous or nonproteinaceous solutes. In preferred embodiments, the antagonist will be purified (1) to greater than 95% by weight of antagonist as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antagonist includes the antagonist in situ within recombinant cells since at least one component of the antagonist's natural environment will not be present. Ordinarily, however, isolated antagonist will be prepared by at least one purification step.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

The expression "therapeutically effective amount" refers to an amount of the antagonist which is effective for preventing, ameliorating or treating the autoimmune disease in question.

The term "immunosuppressive agent" as used herein for adjunct therapy refers to substances that act to suppress or mask the immune system of the mammal being treated herein. This would include substances that suppress cytokine production, downregulate or suppress self-antigen expression, or mask the MHC antigens. Examples of such agents include 2-amino-6-aryl-5-substituted pyrimidines (see U.S. Pat. No. 4,665,077, the disclosure of which is incorporated herein by reference); nonsteroidal antiinflammatory drugs (NSAIDs); azathioprine; cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; methotrexate (oral or subcutaneous); hydroxycloroquine; sulfasalazine; leflunomide; cytokine or cytokine receptor antagonists including anti-interferon-γ, -β, or -α antibodies, anti-tumor necrosis factor-s antibodies (infliximab or adalimumab), anti-TNFα immunoahesin (etanercept), anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (Cohen et al., U.S. Pat. No. 5,114, 721); T-cell receptor fragments (Offner et al., *Science,* 251: 430-432 (1991); WO 90/11294; Ianeway, *Nature,* 341: 482 (1989); and WO 91/01133); and T cell receptor antibodies (EP 340,109) such as T10B9.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes.

II. Production of Antagonists

The methods and articles of manufacture of the present invention use, or incorporate, an antagonist which binds to a B cell surface marker. Accordingly, methods for generating such antagonists will be described here.

The B cell surface marker to be used for production of, or screening for, antagonist(s) may be, e.g., a soluble form of the antigen or a portion thereof, containing the desired epitope. Alternatively, or additionally, cells expressing the B cell surface marker at their cell surface can be used to generate, or screen for, antagonist(s). Other forms of the B cell surface marker useful for generating antagonists will be apparent to those skilled in the art. Preferably, the B cell surface marker is the CD20 antigen.

While the preferred antagonist is an antibody, antagonists other than antibodies are contemplated herein. For example, the antagonist may comprise a small molecule antagonist optionally fused to, or conjugated with, a cytotoxic agent (such as those described herein). Libraries of small molecules may be screened against the B cell surface marker of interest herein in order to identify a small molecule which binds to that antigen. The small molecule may further be screened for its antagonistic properties and/or conjugated with a cytotoxic agent.

The antagonist may also be a peptide generated by rational design or by phage display (see, e.g., WO98/35036 published 13 Aug. 1998). In one embodiment, the molecule of choice may be a "CDR mimic" or antibody analogue designed based on the CDRs of an antibody. While such peptides may be antagonistic by themselves, the peptide may optionally be fused to a cytotoxic agent so as to add or enhance antagonistic properties of the peptide.

A description follows as to exemplary techniques for the production of the antibody antagonists used in accordance with the present invention.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001

(1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, antibodies or antibody fragments can be isolated from antibody phage libraries generated using the techniques described in McCafferty et al., *Nature*, 348: 552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH1 and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al. *J. Immunol.* 147: 60 (1991).

III. Conjugates and Other Modifications of the Antagonist

The antagonist used in the methods or included in the articles of manufacture herein is optionally conjugated to a cytotoxic agent.

Chemotherapeutic agents useful in the generation of such antagonist-cytotoxic agent conjugates have been described above.

Conjugates of an antagonist and one or more small molecule toxins, such as a calicheamicin, a maytansine (U.S. Pat. No. 5,208,020), a trichothene, and CC 1065 are also contemplated herein. In one embodiment of the invention, the antagonist is conjugated to one or more maytansine molecules (e.g. about 1 to about 10 maytansine molecules per antagonist molecule). Maytansine may, for example, be converted to May-SS-Me which may be reduced to May-SH3 and reacted with modified antagonist (Chari et al. *Cancer Research* 52: 127-131 (1992)) to generate a maytansinoid-antagonist conjugate.

Alternatively, the antagonist is conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al. *Cancer Research* 53: 3336-3342 (1993) and Lode et al. *Cancer Research* 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates antagonist conjugated with a compound with nucleolytic activity (e.g. a ribonuclease or a DNA endonuclease such as a deoxyribonuclease; DNase).

A variety of radioactive isotopes are available for the production of radioconjugated antagonists. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antagonist and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antagonist. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antagonist and cytotoxic agent may be made, e.g. by recombinant techniques or peptide synthesis.

In yet another embodiment, the antagonist may be conjugated to a "receptor" (such streptavidin) for utilization in tumor pretargeting wherein the antagonist-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antagonists of the present invention may also be conjugated with a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antagonist-abzyme conjugates can be prepared as described herein for delivery of the abzyme to a tumor cell population.

The enzymes of this invention can be covalently bound to the antagonist by techniques well known in the art such as the use of the heterobifunctional crosslinking reagents discussed above. Alternatively, fusion proteins comprising at least the antigen binding region of an antagonist of the invention linked to at least a functionally active portion of an enzyme of the invention can be constructed using recombinant DNA techniques well known in the art (see, e.g., Neuberger et al., *Nature*, 312: 604-608 (1984)).

Other modifications of the antagonist are contemplated herein. For example, the antagonist may be linked to one of a variety of nonproteinaceous polymers, e.g., polyethylene glycol, polypropylene glycol, polyoxyalkylenes, or copolymers of polyethylene glycol and polypropylene glycol.

The antagonists disclosed herein may also be formulated as liposomes. Liposomes containing the antagonist are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

Amino acid sequence modification(s) of protein or peptide antagonists described herein are contemplated. For example, it may be desirable to improve the binding affinity and/or other biological properties of the antagonist. Amino acid sequence variants of the antagonist are prepared by introducing appropriate nucleotide changes into the antagonist nucleic acid, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics. The amino acid changes also may alter post-translational processes of the antagonist, such as changing the number or position of glycosylation sites.

A useful method for identification of certain residues or regions of the antagonist that are preferred locations for mutagenesis is called "alanine scanning mutagenesis" as described by Cunningham and Wells *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antagonist variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by different residue. The sites of greatest interest for substitutional mutagenesis of antibody antagonists include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antagonist are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antagonist also may be substituted, generally with serine, to improve the oxidative stability of the molecule and prevent aberrant crosslinking. Conversely, cysteine bond(s) may be added to the antagonist to improve its stability (particularly where the antagonist is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antagonist alters the original glycosylation pattern of the antagonist. By altering is meant deleting one or more carbohydrate moieties found in the antagonist, and/or adding one or more glycosylation sites that are not present in the antagonist.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antagonist is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antagonist (for O-linked glycosylation sites).

Nucleic acid molecules encoding amino acid sequence variants of the antagonist are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

It may be desirable to modify the antagonist of the invention with respect to effector function, e.g. so as to enhance antigen-dependent cell-mediated cyotoxicity (ADCC) and/or complement dependent cytotoxicity (CDC) of the antagonist.

This may be achieved by introducing one or more amino acid substitutions in an Fc region of an antibody antagonist. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

To increase the serum half life of the antagonist, one may incorporate a salvage receptor binding epitope into the antagonist (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

IV. Pharmaceutical Formulations

Therapeutic formulations of the antagonists used in accordance with the present invention are prepared for storage by mixing an antagonist having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418, expressly incorporated herein by reference. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5.

Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antagonist present in the formulation, the type of disease or disorder or treatment, and other factors discussed above. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

V. Treatment with the Antagonist

The present invention concerns therapy of a subpopulation of mammals, especially humans, with, or susceptible to, an autoimmune disease, who experience an inadequate response to previous or current treatment with a TNFα-inhibitor. Generally, the mammal to be treated herein will be identified following therapy with one or more treatments with one or more TNFα-inhibitor(s) such as Etanercept (ENBREL®), Infliximab (REMICADE®) or Adalimumab (HUMIRA™), as experiencing an inadequate response to previous or current treatment with a TNFα-inhibitor because of toxicity and/or inadequate efficacy. However, the invention is not limited to a prior therapy step with such a TNFα-inhibitor; for instance, the patient may be considered to be prone to experience a toxicity, e.g. cardiac toxicity, with a TNFα-inhibitor before therapy therewith has begun, or the patient may be determined to be one who is unlikely to respond to therapy with a TNFα-inhibitor.

The various autoimmune diseases to be treated herein are listed in the definitions section above. The preferred indications herein are rheumatoid arthritis, psoriatic arthritis, or Crohn's disease.

Generally, the mammal treated herein will not be suffering from a B-cell malignancy.

According to one embodiment of the invention contemplated herein, the therapeutic approach will reduce negative side effects (such as infections, heart failure and demyelination) associated with therapy with a TNFα-inhibitor.

The composition comprising an antagonist which binds to a B cell surface marker will be formulated, dosed, and administered in a fashion consistent with good medical practice. Factors for consideration in this context include the particular disease or disorder being treated, the particular mammal being treated, the clinical condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

As a general proposition, the therapeutically effective amount of the antagonist administered parenterally per dose will be in the range of about 0.1 to 20 mg/kg of patient body weight per day, with the typical initial range of antagonist used being in the range of about 2 to 10 mg/kg.

The preferred antagonist is an antibody, e.g. an antibody such as RITUXAN®, which is not conjugated to a cytotoxic agent. Suitable dosages for an unconjugated antibody are, for example, in the range from about 20 mg/m$^2$ to about 1000 mg/m$^2$. In one embodiment, the dosage of the antibody differs from that presently recommended for RITUXAN®. For example, one may administer to the patient one or more doses of substantially less than 375 mg/m$^2$ of the antibody, e.g. where the dose is in the range from about 20 mg/m$^2$ to about 250 mg/m$^2$, for example from about 50 mg/m$^2$ to about 200 mg/m$^2$.

Exemplary dosage regimens include 375 mg/m2 weekly× 4; or 1000 mg×2 (e.g. on days 1 and 15).

Moreover, one may administer one or more initial dose(s) of the antibody followed by one or more subsequent dose(s), wherein the mg/m$^2$ dose of the antibody in the subsequent dose(s) exceeds the mg/m$^2$ dose of the antibody in the initial dose(s). For example, the initial dose may be in the range from about 20 mg/m$^2$ to about 250 mg/m$^2$ (e.g. from about 50 mg/m$^2$ to about 200 mg/m$^2$) and the subsequent dose may be in the range from about 250 mg/m$^2$ to about 1000 mg/m$^2$.

As noted above, however, these suggested amounts of antagonist are subject to a great deal of therapeutic discretion. The key factor in selecting an appropriate dose and scheduling is the result obtained, as indicated above. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

The antagonist is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antagonist may suitably be administered by pulse infusion, e.g., with declining doses of the antagonist. Preferably the dosing is given by injections, most preferably intravenous or subcutaneous injections, depending in part on whether the administration is brief or chronic.

One may administer other compounds, such as cytotoxic agents, chemotherapeutic agents, immunosuppressive agents and/or cytokines with the antagonists herein. The combined administration includes coadministration, using separate formulations or a single pharmaceutical formulation, and consecutive administration in either order, wherein preferably there is a time period while both (or all) active agents simultaneously exert their biological activities. For RA, and other autoimmune diseases, the antagonist (e.g. CD20 antibody) may be combined with any one or more of disease-modifying antirheumatic drugs (DMARDs) such as hydroxycloroquine, sulfasalazine, methotrexate, leflunomide, azathioprine, D-penicillamine, Gold (oral), Gold (intramuscular), minocycline, cyclosporine, Staphylococcal protein A immunoadsorption; intravenous immunoglobulin (IVIG); nonsteroidal antiinflammatory drugs (NSAIDs); glucocorticoid (e.g. via joint injection); corticosteroid (e.g. methylprednisolone and/ or prednisone); folate etc. Preferably, a TNFα-inhibitor is not administered to the mammal during the period of treatment with the CD20 antagonist.

Aside from administration of protein antagonists to the patient the present application contemplates administration of antagonists by gene therapy. Such administration of nucleic acid encoding the antagonist is encompassed by the expression "administering a therapeutically effective amount of an antagonist". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

Further details of the invention are illustrated by the following non-limiting Examples. The disclosures of all citations in the specification are expressly incorporated herein by reference.

EXAMPLE 1

A patient with active rheumatoid arthritis who has an inadequate response to one or more TNFα-inhibitor therapies is treated with an antibody that binds the B-cell surface antigen, CD20.

Candidates for therapy according to this example include those who have experienced an inadequate response to previous or current treatment with etanercept, infliximab and/or adalimumab because of toxicity or inadequate efficacy (etanercept for ≧3 months at 25 mg twice a week or at least 4 infusions of infliximab at ≧3 mg/kg).

Patients may have swollen joint count (SJC)≧8 (66 joint count), and tender joint count (TJC)≧8 (68 joint count) at screening and randomization; either CRP≧1.5 mg/dl (15 mg/L) or ESR≧28 mm/h; and/or radiographic evidence of at least one joint with definite erosion attributable to rheumatoid arthritis, as determined by the central reading site (any joint of the hands, wrists or feet can be considered with the exception of the DIP joints of the hands).

The CD20 antibody used for therapy may be Rituximab (commercially available from Genentech, Inc.) or humanized 2H7 v16.

Patients are treated with a therapeutically effective dose of the CD20 antibody, for instance, 1000 mg i.v. on Days 1 and 15, or 375 mg/m2 i.v. weekly×4.

Patients may also receive concomitant MTX (10-25 mg/week per oral (p.o.) or parenteral), together with a corticosteroid regimen consisting of methylprednisolone 100 mg i.v. 30 minutes prior to infusions of the CD20 antibody and prednisone 60 mg p.o. on Days 2-7, 30 mg p.o. Days 8-14, returning to baseline dose by Day 16. Patients may also receive folate (5 mg/week) given as either a single dose or as divided daily doses. Patients optionally continue to receive any background corticosteroid (≦10 mg/d prednisone or equivalent) throughout the treatment period.

The primary endpoint may be the proportion of patients with an ACR20 response at Week 24 using a Cochran-Mantel-Haenszel (CMH) test for comparing group differences, adjusted for rheumatoid factor and region.

Potential secondary endpoints include:

1. Proportion of patients with ACR50 and 70 responses at Week 24. These may be analyzed as specified for the primary endpoint.

2. Change in Disease Activity Score (DAS) from screening to Week 24. These may be assessed using an ANOVA model with baseline DAS, rheumatoid factor, and treatment as terms in the model.

3. Categorical DAS responders (EULAR response) at Week 24. These may be assessed using a CMH test adjusted for rheumatoid factor.

4. Changes from screening in ACR core set (SJC, TJC, patient's and physician's global assessments, HAQ, pain, CRP, and ESR). Descriptive statistics may be reported for these parameters.

5. Changes from screening in SF-36. Descriptive statistics may be reported for the 8 domain scores and the mental and physical component scores. In addition, the mental and physical component scores may be further categorized and analyzed.

6. Change in modified Sharp radiographic total score, erosion score, and joint space narrowing score. These may be analyzed using continuous or categorical methodology, as appropriate.

Exploratory endpoints and analysis may involve:

ACR(20/50/70 and ACR n) and change in DAS responses over Weeks 8, 12, 16, 20, 24 and beyond will be assessed using a binary or continuous repeated measures model, as appropriate. Exploratory radiographic analyses including proportion of patients with no erosive progression may be assessed at weeks 24 and beyond.

Further exploratory endpoints (for example complete clinical response, disease free period) will be analyzed descriptively as part of the extended observation period.

Changes from Screen in FACIT-F fatigue will be analyzed with descriptive statistics.

Therapy of RA with the CD20 antibody in patients with an inadequate response to TNFα inhibitor therapy as described above will result in a beneficial clinical response according to any one or more of the endpoints noted above.

What is claimed is:

1. A method of treating rheumatoid arthritis in a human patient who experiences an inadequate response to a TNFα-inhibitor, comprising administering to the patient an antibody that binds to CD20, wherein the antibody is administered as two intravenous doses of 1000 mg.

2. A method of treating rheumatoid arthritis in a human patient who experiences an inadequate response to a TNFα-inhibitor, comprising administering to the patient an antibody which binds to CD20 in an amount that is effective to provide an ACR50 response at week 24, ACR70 response at week 24, or no erosive progression at weeks 24 and beyond, wherein the antibody is administered as two intravenous doses of 1000 mg.

3. The method of claim 2 wherein the antibody comprises rituximab.

4. The method of claim 2 wherein the patient is further treated with concomitant methotrexate (MTX).

5. The method of claim 4 wherein the patient is further treated with a corticosteroid regimen.

6. The method of claim 5 wherein the corticosteroid regimen consists of methylprednisolone and prednisone.

7. The method of claim 2 wherein the CD20 antibody is the only B-cell surface marker antibody administered to the patient.

8. A method of treating rheumatoid arthritis in a human patient who experiences an inadequate response to a TNFα-inhibitor, comprising administering to the patient rituximab, wherein rituximab is administered as two intravenous doses of 1000 mg.

9. The method of claim 8 further comprising administering methotrexate to the patient.

10. A method of treating rheumatoid arthritis in a human patient who experiences an inadequate response to a TNFα-inhibitor, comprising administering to the patient rituximab, and methotrexate, wherein the patient has no erosive progression at weeks 24 and beyond, and wherein rituximab is administered as two intravenous doses of 1000 mg.

11. A method of achieving a clinical response selected from the group consisting of ACR50 response at week 24, ACR70 response at week 24, and no erosive progression at weeks 24 and beyond, in a human rheumatoid arthritis patient who experiences an inadequate response to a TNFα-inhibitor, comprising administering to the patient rituximab, and methotrexate, wherein rituximab is administered as two intravenous doses of 1000 mg.

12. The method of claim 11 wherein the clinical response is ACR50 response at week 24.

13. The method of claim 11 wherein the clinical response is ACR70 response at week 24.

14. The method of claim 11 wherein the clinical response is no erosive progression at weeks 24 and beyond.

* * * * *

SEQUENCE LISTING

```
<160> NUMBER OF SEQ ID NOS: 4

<210> SEQ ID NO 1
<211> LENGTH: 107
<212> TYPE: PRT
<213> ORGANISM: Artificial sequence
<220> FEATURE:
<223> OTHER INFORMATION: humanized sequence

<400> SEQUENCE: 1

Asp Ile Gln Met Thr Gln Ser Pro Ser Ser Leu Ser Ala Ser Val
  1               5                  10                  15

Gly Asp Arg Val Thr Ile Thr Cys Arg Ala Ser Ser Ser Val Ser
                 20                  25                  30

Tyr Met His Trp Tyr Gln Gln Lys Pro Gly Lys Ala Pro Lys Pro
                 35                  40                  45

Leu Ile Tyr Ala Pro Ser Asn Leu Ala Ser Gly Val Pro Ser Arg
                 50                  55                  60
```

```
Phe Ser Gly Ser Gly Ser Gly Thr Asp Phe Thr Leu Thr Ile Ser
            65                  70                  75

Ser Leu Gln Pro Glu Asp Phe Ala Thr Tyr Tyr Cys Gln Gln Trp
            80                  85                  90

Ser Phe Asn Pro Pro Thr Phe Gly Gln Gly Thr Lys Val Glu Ile
            95                  100                 105

Lys Arg

<210> SEQ ID NO 2
<211> LENGTH: 122
<212> TYPE: PRT
<213> ORGANISM: Artificial sequence
<220> FEATURE:
<223> OTHER INFORMATION: humanized sequence

<400> SEQUENCE: 2

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Asp Thr Ser Tyr
            50                  55                  60

Asn Gln Lys Phe Lys Gly Arg Phe Thr Ile Ser Val Asp Lys Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Asn Ser
            95                  100                 105

Tyr Trp Tyr Phe Asp Val Trp Gly Gln Gly Thr Leu Val Thr Val
            110                 115                 120

Ser Ser

<210> SEQ ID NO 3
<211> LENGTH: 213
<212> TYPE: PRT
<213> ORGANISM: Artificial sequence
<220> FEATURE:
<223> OTHER INFORMATION: humanized sequence

<400> SEQUENCE: 3

Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Ser Val Ser
            20                  25                  30

Tyr Met His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
            50                  55                  60

Phe Ser Gly Ser Gly Ser Gly Thr Asp Phe Thr Leu Thr Ile Ser
            65                  70                  75

Ser Leu Gln Pro Glu Asp Phe Ala Thr Tyr Tyr Cys Gln Gln Trp
            80                  85                  90

Ser Phe Asn Pro Pro Thr Phe Gly Gln Gly Thr Lys Val Glu Ile
            95                  100                 105

Lys Arg Thr Val Ala Ala Pro Ser Val Phe Ile Phe Pro Pro Ser
```

```
                           110                 115                 120
Asp Glu Gln Leu Lys Ser Gly Thr Ala Ser Val Val Cys Leu Leu
                125                 130                 135

Asn Asn Phe Tyr Pro Arg Glu Ala Lys Val Gln Trp Lys Val Asp
                140                 145                 150

Asn Ala Leu Gln Ser Gly Asn Ser Gln Glu Ser Val Thr Glu Gln
                155                 160                 165

Asp Ser Lys Asp Ser Thr Tyr Ser Leu Ser Ser Thr Leu Thr Leu
                170                 175                 180

Ser Lys Ala Asp Tyr Glu Lys His Lys Val Tyr Ala Cys Glu Val
                185                 190                 195

Thr His Gln Gly Leu Ser Ser Pro Val Thr Lys Ser Phe Asn Arg
                200                 205                 210

Gly Glu Cys

<210> SEQ ID NO 4
<211> LENGTH: 452
<212> TYPE: PRT
<213> ORGANISM: Artificial sequence
<220> FEATURE:
<223> OTHER INFORMATION: humanized sequence

<400> SEQUENCE: 4

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Asp Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Asn Ser
                95                  100                 105

Tyr Trp Tyr Phe Asp Val Trp Gly Gln Gly Thr Leu Val Thr Val
                110                 115                 120

Ser Ser Ala Ser Thr Lys Gly Pro Ser Val Phe Pro Leu Ala Pro
                125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240
```

-continued

```
Gly Gly Pro Ser Val Phe Leu Phe Pro Pro Lys Pro Lys Asp Thr
            245                 250                 255
Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln
            290                 295                 300
Tyr Asn Ser Thr Tyr Arg Val Val Ser Val Leu Thr Val Leu His
            305                 310                 315
Gln Asp Trp Leu Asn Gly Lys Glu Tyr Lys Cys Lys Val Ser Asn
            320                 325                 330
Lys Ala Leu Pro Ala Pro Ile Glu Lys Thr Ile Ser Lys Ala Lys
            335                 340                 345
Gly Gln Pro Arg Glu Pro Gln Val Tyr Thr Leu Pro Pro Ser Arg
            350                 355                 360
Glu Glu Met Thr Lys Asn Gln Val Ser Leu Thr Cys Leu Val Lys
            365                 370                 375
Gly Phe Tyr Pro Ser Asp Ile Ala Val Glu Trp Glu Ser Asn Gly
            380                 385                 390
Gln Pro Glu Asn Asn Tyr Lys Thr Thr Pro Pro Val Leu Asp Ser
            395                 400                 405
Asp Gly Ser Phe Phe Leu Tyr Ser Lys Leu Thr Val Asp Lys Ser
            410                 415                 420
Arg Trp Gln Gln Gly Asn Val Phe Ser Cys Ser Val Met His Glu
            425                 430                 435
Ala Leu His Asn His Tyr Thr Gln Lys Ser Leu Ser Leu Ser Pro
            440                 445                 450
Gly Lys
```